United States Patent
Hunter et al.

(10) Patent No.: US 10,810,284 B2
(45) Date of Patent: Oct. 20, 2020

(54) SYSTEMS AND METHODS FOR PROVIDING VIRTUAL ACCESS TO A SURGICAL CONSOLE

(71) Applicant: Johnson & Johnson Surgical Vision, Inc., Santa Ana, CA (US)

(72) Inventors: Timothy L. Hunter, Corona Del Mar, CA (US); Catherine P. Ha, Fountain Valley, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 315 days.

(21) Appl. No.: 15/349,164

(22) Filed: Nov. 11, 2016

(65) Prior Publication Data

US 2017/0132385 A1    May 11, 2017

Related U.S. Application Data

(60) Provisional application No. 62/254,107, filed on Nov. 11, 2015.

(51) Int. Cl.

| | |
|---|---|
| G06F 19/00 | (2018.01) |
| G16H 20/40 | (2018.01) |
| G16H 40/63 | (2018.01) |
| G06F 9/451 | (2018.01) |
| G16H 40/67 | (2018.01) |
| A61B 34/00 | (2016.01) |
| A61F 9/007 | (2006.01) |

(Continued)

(52) U.S. Cl.
CPC .......... *G06F 19/3418* (2013.01); *A61B 34/25* (2016.02); *A61F 9/00781* (2013.01); *G06F 9/452* (2018.02); *G16H 40/63* (2018.01); *G16H 40/67* (2018.01); *A61B 2017/00199* (2013.01); *A61B 2034/256* (2016.02); *A61F 9/00745* (2013.01); *A61F 2009/00887* (2013.01); *A61F 2009/00891* (2013.01); *G16H 20/40* (2018.01)

(58) Field of Classification Search
CPC ..... G06F 19/3418; G06F 9/452; A61B 34/25; A61B 2034/256; A61B 2017/00199; A61B 34/30; A61B 34/10; G16H 19/3418; G16H 40/67; G16H 40/63; G16H 20/40; A61F 9/00781; A61F 9/00745; A61F 2009/00887; A61F 2009/00891
See application file for complete search history.

(56) References Cited

U.S. PATENT DOCUMENTS

| | | | |
|---|---|---|---|
| 8,161,195 B2* | 4/2012 | Matesan | H04L 67/1095 709/248 |
| 8,489,999 B2* | 7/2013 | Harvey | G06Q 10/10 715/748 |

(Continued)

OTHER PUBLICATIONS

International Search Report and Written Opinion for Application No. PCT/US2016/061504, dated Feb. 22, 2017, 11 pages.

*Primary Examiner* — Ryan F Pitaro
(74) *Attorney, Agent, or Firm* — Johnson & Johnson Surgical Vision, Inc.

(57) ABSTRACT

A computer-based system and method is provided to allow for virtual access and control of a surgical console. The present invention may provide for the replication of the graphical user interface (GUI) associated with a piece of operating room equipment and the provisioning of the replicated GUI to an internet accessible platform that may act as an access point for a plurality of users.

10 Claims, 22 Drawing Sheets

(51) Int. Cl.
*A61B 17/00* (2006.01)
*A61F 9/008* (2006.01)

(56) References Cited

U.S. PATENT DOCUMENTS

| | | | |
|---|---|---|---|
| 9,395,885 B1* | 7/2016 | Kominac | G06F 3/0484 |
| 2004/0179036 A1* | 9/2004 | Teplov | G06F 3/1454 |
| | | | 715/751 |
| 2006/0149301 A1* | 7/2006 | Claus | A61F 9/00745 |
| | | | 606/169 |
| 2006/0235307 A1* | 10/2006 | Boukhny | A61F 9/00745 |
| | | | 600/471 |
| 2008/0256076 A1* | 10/2008 | Claus | G06F 21/34 |
| 2008/0281301 A1* | 11/2008 | Deboer | G16H 15/00 |
| | | | 606/1 |
| 2008/0316304 A1* | 12/2008 | Claus | G16H 40/63 |
| | | | 348/61 |
| 2009/0049522 A1* | 2/2009 | Claus | G06F 19/00 |
| | | | 726/4 |
| 2009/0103785 A1* | 4/2009 | Pedroza | G07C 9/00158 |
| | | | 382/117 |
| 2009/0171328 A1* | 7/2009 | Horvath | A61B 34/25 |
| | | | 606/10 |
| 2009/0190808 A1* | 7/2009 | Claus | A61B 5/107 |
| | | | 382/128 |
| 2009/0300507 A1* | 12/2009 | Raghavan | G06F 19/3418 |
| | | | 715/738 |
| 2009/0306581 A1* | 12/2009 | Claus | A61F 9/00745 |
| | | | 604/22 |
| 2010/0017372 A1* | 1/2010 | Park | G06F 17/30023 |
| | | | 707/E17.014 |
| 2010/0063834 A1* | 3/2010 | Mukherjee | G06Q 50/22 |
| | | | 705/2 |
| 2010/0287127 A1* | 11/2010 | Claus | A61F 9/00745 |
| | | | 706/12 |
| 2011/0118748 A1* | 5/2011 | Itkowitz | A61B 19/2203 |
| | | | 606/130 |
| 2011/0257638 A1* | 10/2011 | Boukhny | A61B 90/36 |
| | | | 606/4 |
| 2011/0276619 A1* | 11/2011 | Khan | H04L 67/141 |
| | | | 709/203 |
| 2012/0151371 A1* | 6/2012 | Kominac | G06F 17/30905 |
| | | | 715/740 |
| 2012/0245576 A1* | 9/2012 | Epstein | A61B 18/1477 |
| | | | 606/33 |
| 2013/0069769 A1* | 3/2013 | Pennington | G08C 17/02 |
| | | | 340/12.28 |
| 2013/0088414 A1* | 4/2013 | Artsyukhovich | G06F 3/14 |
| | | | 345/7 |
| 2013/0090636 A1* | 4/2013 | Patton | A61F 9/00745 |
| | | | 606/6 |
| 2013/0093829 A1* | 4/2013 | Rosenblatt | G09B 5/00 |
| | | | 348/14.01 |
| 2013/0290857 A1* | 10/2013 | Beveridge | G06F 3/0484 |
| | | | 715/740 |
| 2014/0002361 A1* | 1/2014 | Ballard | G06F 3/03543 |
| | | | 345/163 |
| 2014/0123237 A1* | 5/2014 | Gaudet | H04L 63/08 |
| | | | 726/4 |
| 2014/0142592 A1* | 5/2014 | Moon | A61B 34/30 |
| | | | 606/130 |
| 2014/0222942 A1 | 8/2014 | Lin et al. | |
| 2014/0267658 A1* | 9/2014 | Speier | H04N 7/181 |
| | | | 348/72 |
| 2014/0278473 A1* | 9/2014 | Duff | G16H 40/63 |
| | | | 705/2 |
| 2014/0280474 A1* | 9/2014 | Lynn | H04L 67/10 |
| | | | 709/203 |
| 2015/0012831 A1* | 1/2015 | Boggess | G06F 3/1454 |
| | | | 715/733 |
| 2015/0031993 A1* | 1/2015 | Buckland | A61B 3/102 |
| | | | 600/425 |
| 2015/0033128 A1* | 1/2015 | Curd | G06F 3/167 |
| | | | 715/728 |
| 2015/0073816 A1 | 3/2015 | Ha et al. | |
| 2015/0310171 A1* | 10/2015 | Hajishah | A61B 34/10 |
| | | | 715/771 |
| 2016/0330266 A1* | 11/2016 | Bakhmutov | H04L 67/025 |
| 2017/0242557 A1* | 8/2017 | Rotschield | G06F 3/04817 |
| 2017/0344331 A1* | 11/2017 | Singh | G06F 3/1454 |
| 2018/0039747 A1* | 2/2018 | Chong | G06Q 10/06 |

\* cited by examiner

SYSTEMS AND METHODS FOR PROVIDING VIRTUAL ACCESS TO A SURGICAL CONSOLE

CROSS-REFERENCE TO RELATED APPLICATIONS

This application claims the benefit under 35 U.S.C. § 119(e) of U.S. Provisional Patent Application No. 62/254,107, filed Nov. 11, 2015, the full disclosures of which are incorporated herein by reference.

TECHNICAL FIELD OF THE INVENTION

The present invention is generally related to methods, devices, and systems related to apparatuses used in all types of surgery. In particular, the disclosed methods, devices, and systems may be used to improve practices in surgeries such as cataract, Lasik, laser cataract, glaucoma, and the like.

BACKGROUND

To perform procedures on the eye, a surgeon often utilizes a computer-controlled system of specialized equipment called a phacoemulsification system to, for example, ultrasonically emulsify and aspirate the natural lens of the eye prior to inserting the IOL. Phacoemulsification systems use various computer programs for performing various tasks, controlled in part by adjusting settings of the programs to drive motors and pumps, for example, to emulsify and aspirate the subject lens material and to do other tasks necessary to complete the surgery. Different phacoemulsification systems may provide different programs. Further, different programs may be used in different situations. The program settings selected typically take into account the particular subject eye on which surgery is performed based for example on measurements of the eye, grade of cataract, and various other aspects of the patient's physiology.

The duration of a surgical procedure commonly varies from about five to about forty minutes or more. Information pertaining to the procedure is generally monitored and recorded by equipment in the operating room or by operating room staff during the procedure. Among the equipment used in the operating, the phacoemulsification system is generally programmed prior to use to provide for performance particulars specific to the surgeon and/or the patient. During a procedure, information pre-programmed into the surgical console may control features associated with the amount of energy applied to emulsify a lens, the amount of vacuum applied to aspirate, the flow rate, the view of the operating field, the sensitivity and/or operation of an associated foot pedal, and the like.

The pre-programming of the console may occur between each use by a particular surgeon or as between each patient. This is often a time consuming process which leads to more inefficient use of the surgical console, as well as the associated operating room, and to the possible introduction of errors. Such pre-programming errors may be the result of staff entering a surgeon's designated preferences and/or rushing to speed the time of such data entry between scheduled surgical procedures using the same surgical console.

Further, if a surgeon would like to pre-plan or otherwise work with the interface associated with the surgical console prior to beginning a procedure, he or she must wait until the console is out of use. Such a period of time my not occur during the working hours of the surgeon or during any convenient time available to the surgeon. Similarly, any user of the console who is unfamiliar with every aspect of the user interface associated with the surgical console, whether because they require more training, are unfamiliar with recent updates, or are in an academic learning environment, for example, will be similarly limited to the use of the console from both a time prospective and the limitation that only one user may operate the console at a time.

SUMMARY

A computer-based system and method is provided to allow for virtual access and control of a surgical console. The present invention may provide for the replication of the graphical user interface (GUI) associated with a piece of operating room equipment and the provisioning of the replicated GUI to an internet accessible platform that may act as an access point for a plurality of users. Use by more than one user may be simultaneous and may allow for a user to input information which may be provided to the GUI of the physical piece of operating room equipment.

A system for providing a virtual interface with a surgical console, comprising a network attached computer with a processor and a data storage device storing instructions which, when executed on the processor, cause the computer to perform tasks including: obtaining information correspondent to a graphical user interface of a surgical console, populating a virtual graphical user interface resident on a first device remote from the surgical console, receiving, from a second device remote from the surgical console, a request to access the virtual graphical user interface, providing access to the virtual graphic user interface in accordance with the received request, collecting and storing information received from the second device, and providing the information received from the second device to the surgical console.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION

Figure 1:
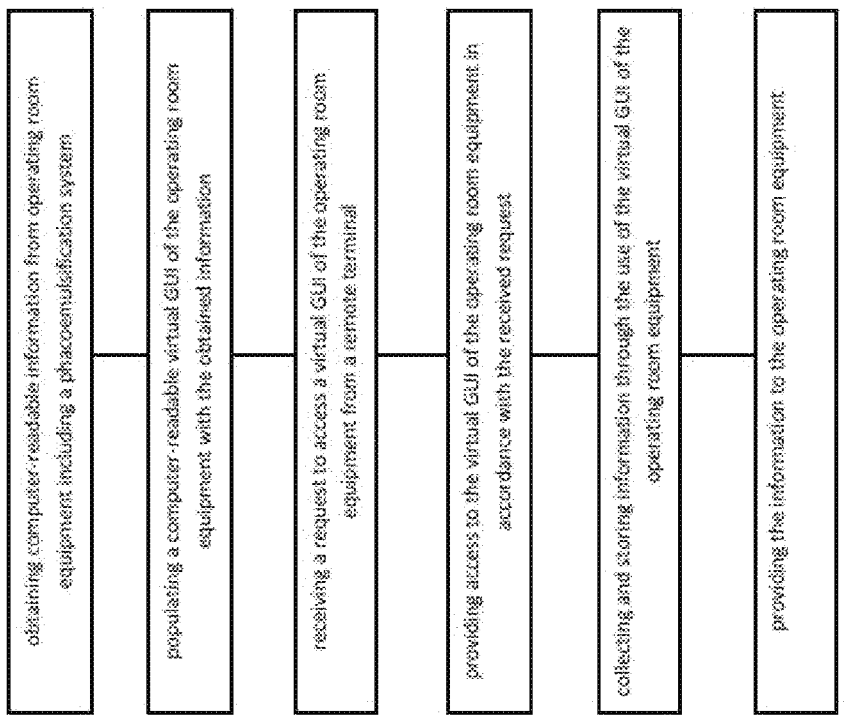
FIG. 1 illustrates an exemplary method for accessing a computer-based virtual operating room system user interface according to the disclosure.

It is to be understood that the figures and descriptions provided herein may have been simplified to illustrate aspects that are relevant for a clear understanding of the herein described apparatus, systems, and methods, while eliminating for the purpose of clarity other aspects that may be found in typical apparatus, systems, and methods. Those of ordinary skill in the pertinent arts may recognize that other or additional elements and/or steps may be desirable and/or necessary to implement the apparatus, systems, and methods described herein. Because such elements and steps are well known to those of ordinary skill, and because they do not facilitate a better understanding of the herein disclosed apparatus, systems, and methods, a discussion of such elements and steps may not be provided herein. However, the present disclosure is deemed to inherently include all such elements, variations, and modifications to the described aspects that would be known to those of ordinary skill in the pertinent arts.

The herein disclosed apparatus, systems, and methods provide to a user with a networked user terminal the ability to virtually interact with one or more devices or systems used in an operating room or similar facility. In embodiments, a user may remotely interface with operating room equipment or virtually with operating room equipment may include one or more of a computer-based phacoemulsification system, a Surgical Media Center (SMC), a laser machine, and the like. Through at least one access device or user terminal, a user may obtain information from the operating room equipment, either directly via their respective network interfaces, or indirectly through a server that obtains information from the operating room equipment. The network interfaces of the operating room equipment and the user terminal may be wired, such as interfaces to Ethernet networks compliant with IEEE 802 network interface standards, or may be wireless, such as air interfaces to cellular data, Bluetooth, or WIFI networks. The user terminal may be a mobile device such as a smart phone, tablet, portable computer, personal desktop computer or the like. The communication network may be private or public, and may include communication over the Internet.

The system thus communicatively couples the user terminal to the operating room equipment or virtual operating room equipment, either directly or through an intermediary server, enabling retrieval of select information of one or more surgical procedures, and allowing the retrieved information to be presented to the user in a predetermined format. The user may be provided a remote and/or virtual view of the GUI associated with selected operating room equipment to obtain operating room equipment settings, surgical case data, energy usage (e.g. phaco energy), and the like. Such views may allow for the virtual use of operating room equipment and may allow for equipment settings to be stored for later use with, for example, a future operation procedure using the operating room equipment. Further, the settings may be modified by the user for use in another procedure.

In embodiments, an application running on the user terminal or on the server may provide access to and use of the GUI of the operating room equipment. As illustrated in FIG. 1, a server communicatively coupled to at least one piece of operating room equipment and having resident thereon at least one application for providing for the replication of derived information, may obtain from the operating room equipment information related to the GUI associated therewith. Utilizing the at least one application and information derived from the operating room equipment, the server may populate at least one virtual GUI resident thereon to provide an updated and substantially matched virtual GUI as compared to the GUI of the operating room equipment. The server may receive a request for access to the virtual GUI and may provide access to the virtual GUI and may use gatekeeper tools known to those skilled in the art to ensure the access granted is authorized and/or authenticated.

Once access is established, certain use and input information may be collected and stored by the server. This collected information may be temporarily stored, for example, and deleted once access to the virtual GUI has ceased, thus eliminating any erroneous use of unwanted information or the dissemination of confidential patient information, for example. The information collected may also be provided back to the operating room equipment and stored locally thereon to allow for the update of information as between the server and the operating room equipment.

Thereby, the system may facilitate surgical procedure efficiency improvement in several ways. For example, a surgeon may manipulate settings of operating room equipment from a remote location and at a time convenient to the surgeon limiting the interruption time created when attempting to change settings directly on the operating room equipment. Such interruption time may take away from the time available to use the operating equipment in surgery and may limit the ability and/or desire of a surgeon to change or double check settings of the operating room equipment available through a GUI not otherwise available through a remote user terminal.

Applications running on or accessible via a user terminal may provide a user with the ability to retrieve networked operating room equipment program settings, such as program settings of a phacoemulsification system. The settings may be saved at the user terminal or at the server. In addition, settings maybe modified for future use. Further, a plurality of groups of settings may be developed by a surgeon, for example based on a plurality of procedures performed on a range of different patients, in different facilities, using various equipment with various staff and/or having other situationally relevant aspects. Groups of settings may be developed for use by the surgeon in different anticipated environments. A select group of settings may be retrieved and used to set up networked operating room equipment before a procedure, based on the peculiarities of the particular operating environment. In an embodiment, a select group of settings may be applied to multiple operating room equipment or systems via the network and user terminal.

In an embodiment, a user terminal may be used to obtain historical data stored on the user terminal, phaco system, server, and/or SMC, to analyze trends of selected cases as an aid to determine modified settings on phaco systems and the like. In an embodiment, a user terminal may be used to obtain stored historical data to analyze trends of select cases. In embodiments, an application on the user terminal or phaco system may use such analyses to make suggestions regarding modifications to user settings on the phaco or other systems to improve technique, outcomes, and/or efficiency. In addition, historical data may be used to suggest other available technology that may be used with the phaco system, or upgrades that may be downloaded to the system, such as to adjust, optimize, and/or improve the user's techniques, outcomes, and/or efficiency.

In an embodiment of the present invention, a networked server in data communication with the networked operating room equipment may be used to obtain and store information of surgical procedures. Applications that operate on the obtained data may then be executed either at the server, or at user terminals, or both, such as distributed applications that have executable elements on both the server and the user terminal. In addition, the server may be arranged to provide a portal for users to access and share their data with other users.

Figure 2:
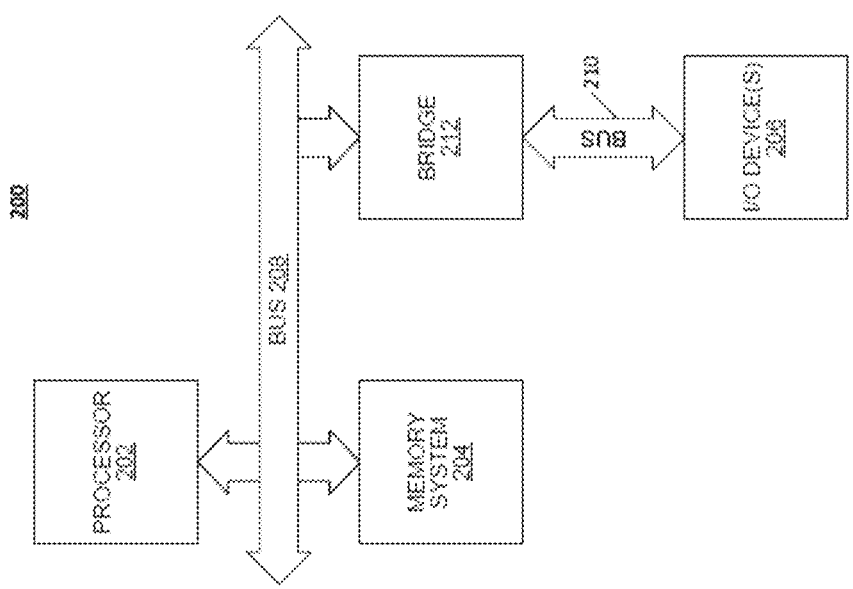
FIG. 2 illustrates an exemplary processor system for facilitating a computer-based virtual operating room system user interface according to the disclosure.

FIG. 2 is an example of a simplified functional block diagram of a computer system 200. The functional descriptions of the present invention can be implemented in hardware, software or some combination thereof. For example, a virtual replication engine of the present invention can be implemented using a computer system.

As shown in FIG. 2, the computer system 200 includes a processor 202, a memory system 204 and one or more input/output (I/O) devices 206 in communication by a communication 'fabric'. The communication fabric can be implemented in a variety of ways and may include one or more computer buses 208, 210 and/or bridge and/or router devices 212 as shown in FIG. 2. The I/O devices 206 can include network adapters and/or mass storage devices from which the computer system 200 can send and receive data for generating and hosting a virtual operating room equipment GUI. The computer system 200 may be in communication with the Internet via the I/O devices 206.

Those of ordinary skill in the art will recognize that many modifications and variations of the present invention may be implemented without departing from the spirit or scope of the invention. Thus, it is intended that the present invention cover the modification and variations of this invention provided they come within the scope of the appended claims and their equivalents.

The various illustrative logics, logical blocks, modules, and engines, described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Figure 3:
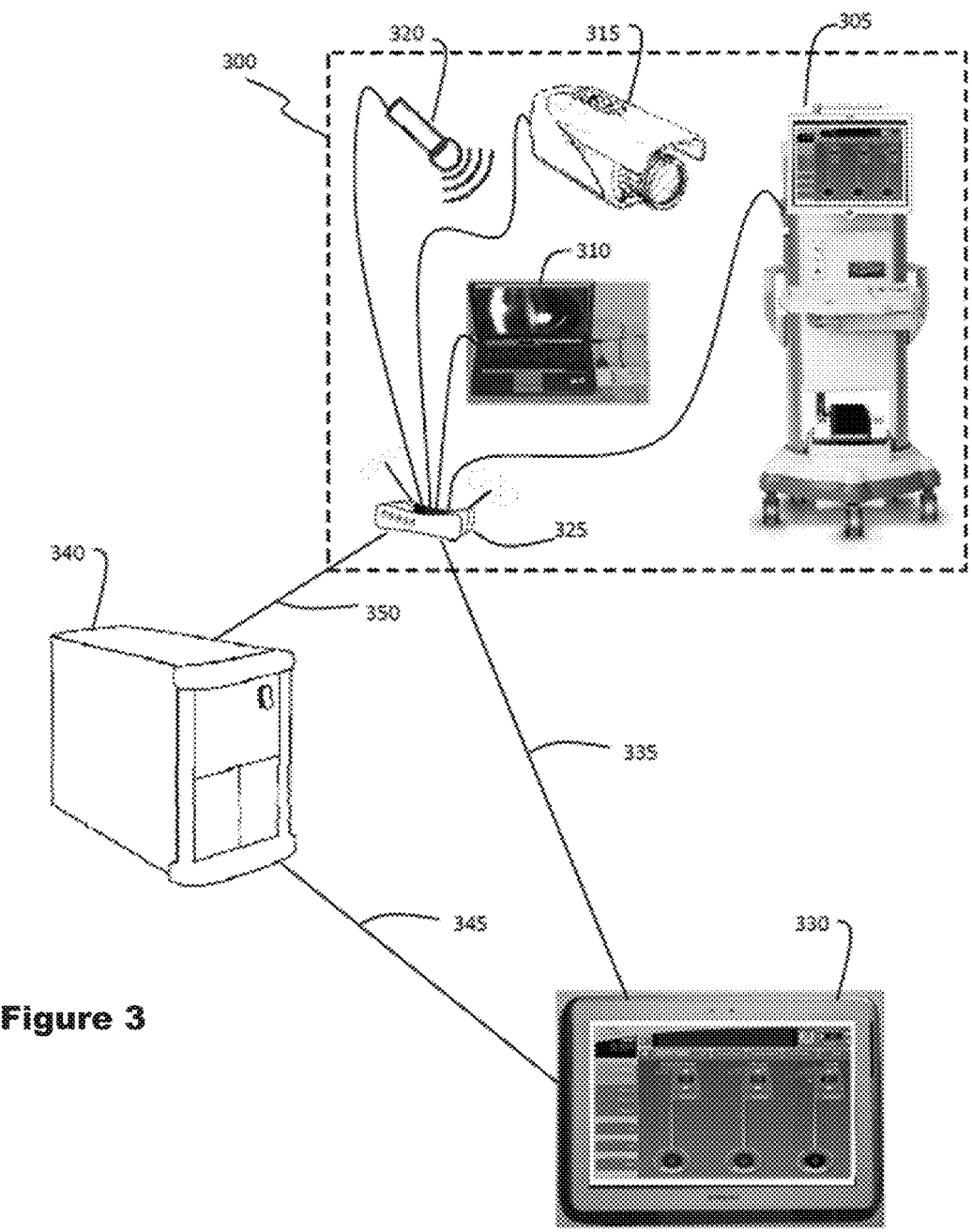
FIG. 3 illustrates an exemplary system for facilitating a computer-based virtual operating room system user interface according to the disclosure.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or actions of a method or algorithm may reside as one or any combination or set of instructions on a machine readable medium and/or computer readable medium Referring now to FIG. 3, operating room equipment, in the form of a cataract operating room support system, for example, is illustrated. Network attached equipment in an operating room 300 in which surgery is performed may include a computer-based phacoemulsification system 305, computer-based surgical media center (SMC) 310, as well as other equipment such as video camera 315 and microphone 320. Other devices (not shown) may also include a microscope and/or additional viewing screens. Each networked device has a network identifier, such as an internet protocol IP address, which may be used to access the device over the network. The equipment may be coupled to router 325, which may perform a network address translation (NAT) function to the operating room equipment coupled thereto, as is known in the art. Computer-readable information may be obtained from the operating room equipment from user terminal 330, either directly via network connection 335, or indirectly via server 340 via network connections 345, 350.

Figure 4:
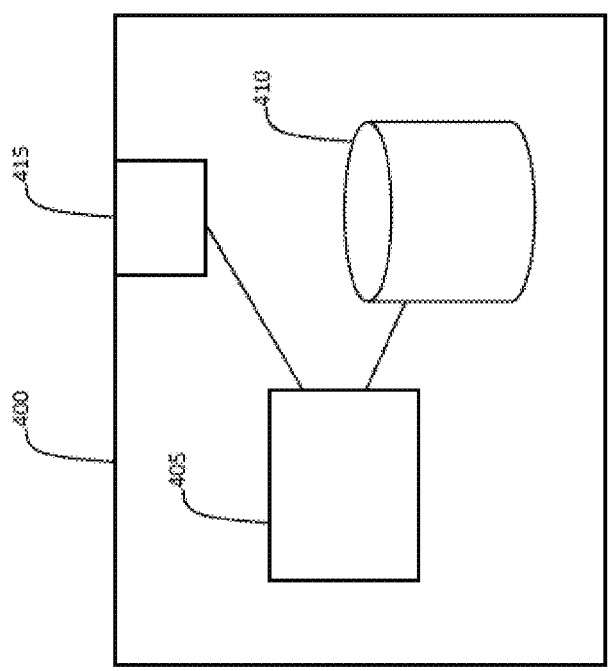
FIG. 4 illustrates an exemplary simplified functional block diagram of a computer system according to the disclosure.

FIG. 4 is illustrative of a computerized device 400 representative of aspects of user terminal 330, server 340, SMC 310 and phaco system 305. Computerized device 400 is capable of executing software, such as an operating system (OS) and a variety of computing applications. The operation of exemplary computerized device 400 is controlled by computer readable instructions stored in a computer readable storage medium 410, such as a hard disk drive (HDD), optical disk such as a CD or DVD, random access memory (RAM), solid state drive, a USB "thumb drive," or the like. Such instructions may be executed within central processing unit (CPU) 405 to cause computerized device 400 to perform operations. Typically, the CPU is implemented in an integrated circuit called a microprocessor. In operation, the CPU fetches, decodes, and executes instructions from storage device 410. Such instructions may be included in software such as an operating system (OS), executable programs such as the herein described applications, and the like.

The user terminal, SMC, and phaco system may also comprise a display for viewing visual output generated by computerized device 400, responsive to operation of the aforementioned computing program, such as an app. Such visual output may include text, graphics, animated graphics, and/or video, for example. The display may be implemented with an LCD or LED-based or other flat panel display, for example.

Network adapter 415 may provide access to a network which may include one or more of a local area network (LAN), wide area network (WAN), Internet, an intranet, an extranet, or the like. The network provides remote access to computerized device 400 for transferring software and information electronically. Additionally, the network may provide for distributed processing, which may involve more than one cooperating computerized devices in performing a task. It is appreciated that the network configurations described are exemplary and other means of establishing communication links between computerized device 400 and remote users may be used. Network interface 415 may communicate with the network using any available wired or wireless technologies. Such technologies may include, by way of non-limiting example, wired and wireless interfaces such as gigabit ethernet, wifi, cellular data, or the like.

It is appreciated that exemplary computerized device 400 is merely illustrative of a computing environment in which the herein described systems and methods may operate, and does not limit the implementation of the herein described systems and methods in computing environments having differing components and configurations. That is to say, the inventive concepts described herein may be implemented in these or other computing environments using these or other components and configurations.

Figure 5:
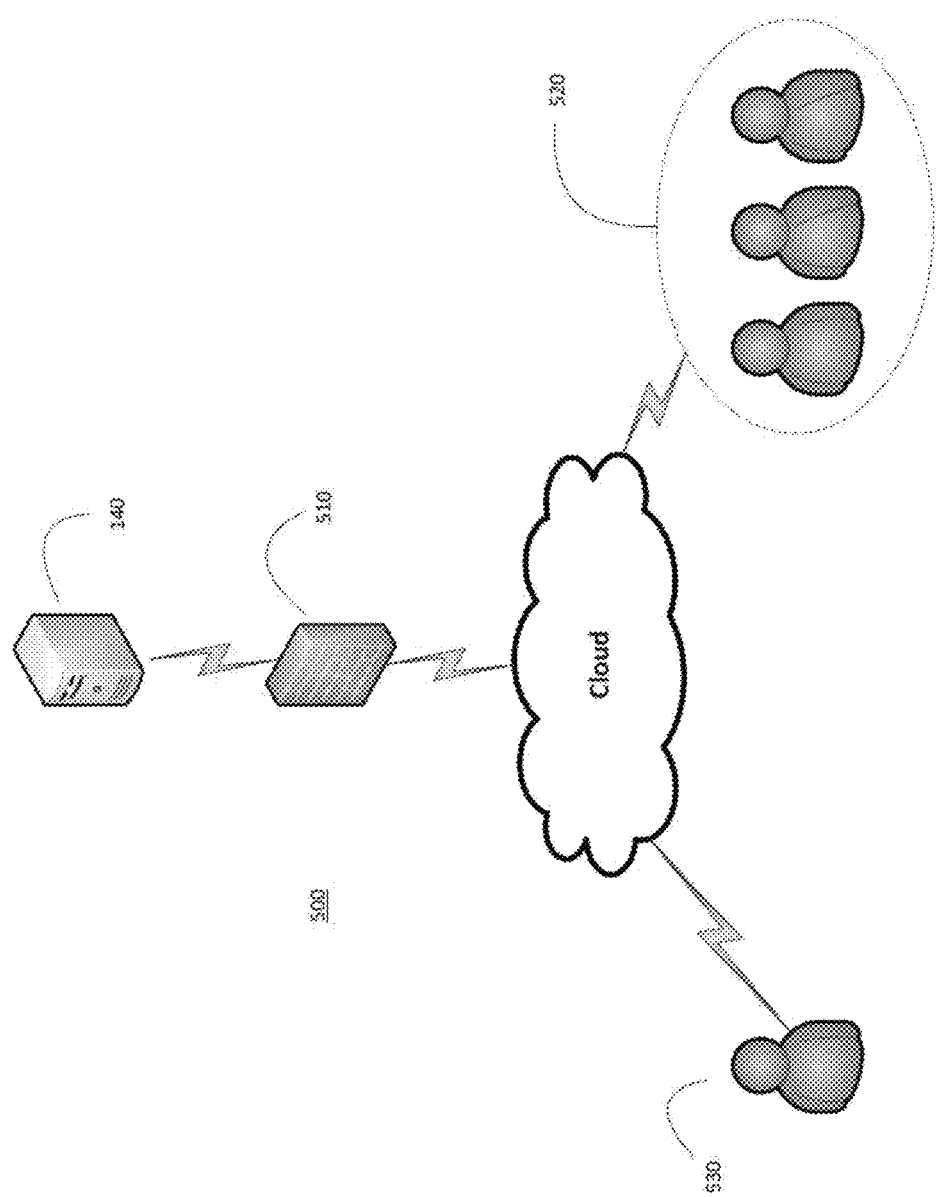
FIG. 5 illustrates an exemplary system for facilitating a computer-based virtual operating room system user interface according to the disclosure.
Figure 6:
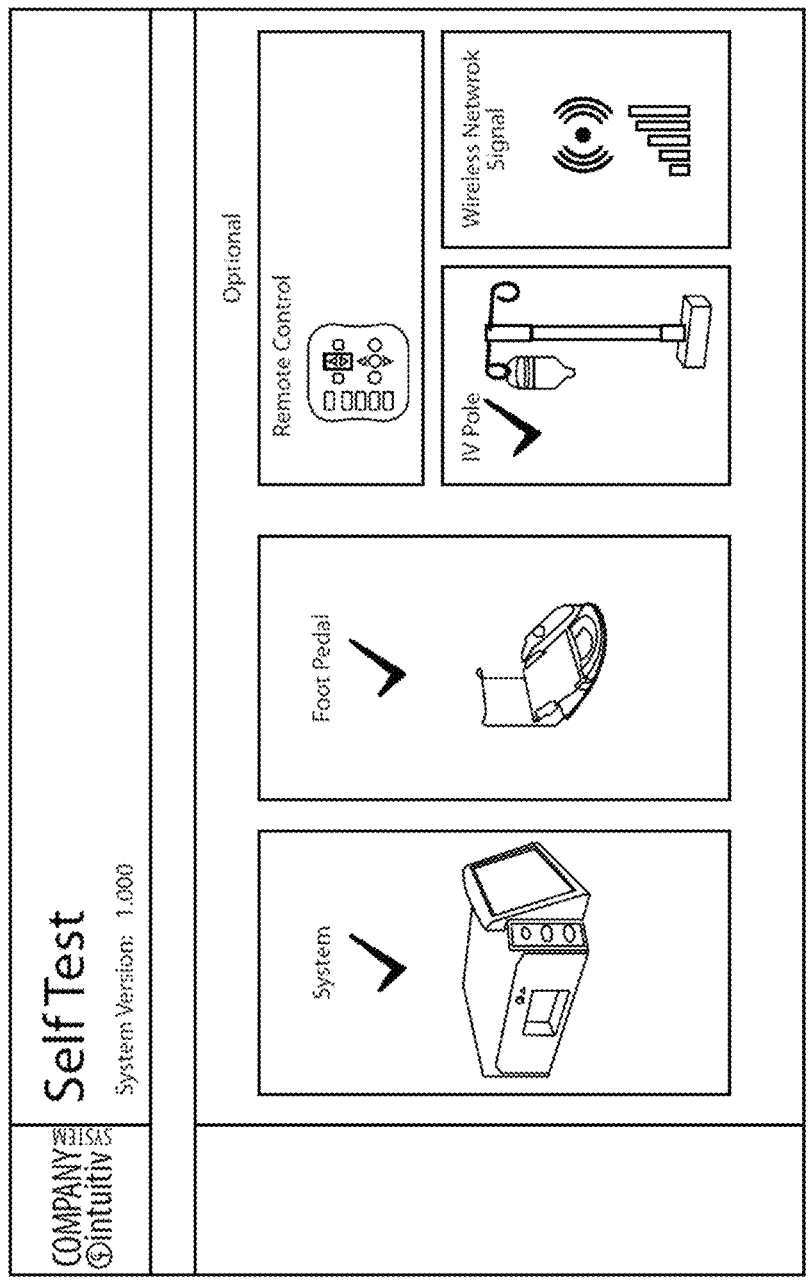
FIGS. 6-22 show exemplary charts and graphs illustrating the display of information provided by the system on a user terminal.

Computerized device 400 may be deployed in networked computing environment such as that illustrated in FIG. 5. In general, the above description for computing system 300 applies to server, user terminal, and computerized operating room equipment coupled to a networked environment, in which the herein described apparatus and methods may be employed. Network communications may use one or more known communication protocols, such as hypertext transfer protocol (HTTP), file transfer protocol (FTP), simple object access protocol (SOAP), wireless application protocol (WAP), or the like. Additionally, the networked computing environment may utilize various data security protocols such as secured socket layer (SSL), pretty good privacy (PGP), virtual private network (VPN) security, or the like. Each network attached device may be provided with an operating system able to support one or more computing and/or communication applications such as a web browser, email, user interfaces, medical device controls, and data analysis and formatting applications and the like discussed herein.

As illustrated in FIG. 5, a firewall 510 may be employed between a public network and users 520 and 530 and may be used to restrict access to at least server 140, for example. Users 520 may be at least two in number and may be related by location, professional affiliation, system authentication credentials, and the like. For example, a sales presentation may be given to a large group of surgeons who may be provided temporary credentialed access to the present invention by the sales person present. Each of users 520 may then access and interface with at least one version of a virtual operating room equipment GUI, a version which may be pre-populated with information representative of at least one selection of settings relative to the use of the operating room equipment wanting to be demonstrated by the sales person. The users 520 may also be a group of students, who may be accessing at least server 140 from different locations at different times, but for whom all share at least a portion of commonality correspondent to the access credentials provided.

Embodiments of the herein disclosed apparatus, systems, and methods may include one or more applications (apps) running on a user terminal or networked server in a computing environment such as that discussed above with respect to FIGS. 3 and 5. The app may interface directly with computer-based devices providing a virtual operating room equipment GUI and may further allow for communication with operating room equipment in the operating room in substantially real time, or may interact with a device through a server.

One or more of the operating room equipment system(s), the server(s), or user terminal(s) may accumulate, or "log", data of a single surgical or a plurality of procedures, and store the data through the virtual operating room equipment GUI. Such data may include information from procedures, settings programmed by a doctor or scrub nurse, etc. Stored data may be shared or transferred between the operating room equipment system(s), the server(s), the SMC(s), and/or user terminal(s). Such sharing or transferring may occur automatically based in a program running on one or more of the operating room equipment system, the server, SMC, and/or the user terminal. Similarly, the sharing and/or transfer of data may occur responsive to a user request or instructions input using the user terminal.

In an embodiment of the present invention, a user of the operating room equipment, such as a doctor, may access a virtual operating room equipment GUI associated with the equipment targeted to be used in the future to review operational controls, tailor equipment performance for a specific patient, adjust certain parameters based on operational preferences, and/or review past equipment settings for comparison to outcome to determine optimal usage parameters. For example, as illustrated in FIGS. 6-22, the virtual operating room equipment GUI of the present invention may provide the user with the same GUI experience remotely from a piece of operating equipment as they would have with the GUI associated directly with the physical operating room equipment. Using eye surgery, and more specifically, cataract surgery, as an example type of procedure, the necessary operating room equipment may include Abbott Medical Optics Inc.'s WHITESTAR Signature® phacoemulsification system or other similar types of systems.

In an exemplary embodiment, a smartphone user terminal may run an app that will access the virtual operating room equipment GUI associated with and mirroring of the GUI associated with the WHITESTAR Signature® phacoemulsification system via a wireless network connection. Utilizing the displayed virtual operating room equipment GUI, the smartphone may retrieve surgical information pertaining to a specific surgeon, for example, and may allow for such information to be changed and/or reviewed. Similarly, the virtual operating room equipment GUI may not collect any specific information prior to being accessed and may, for example, retain information collected only through that particular use.

The use of the virtual operating room equipment GUI may allow for increased efficiency of operating equipment use, eliminate or reduce equipment setup errors, improve user efficiency, and improve surgical outcomes, for example. As discussed herein, the virtual operating room equipment GUI may allow for user to make changes to the operational settings of operating room equipment prior to actually using the equipment and eliminating the need to spend time between surgical use of the equipment to perform the same function.

By way of limiting example, a surgeon may access the virtual operating room equipment GUI in anticipation of providing surgery to a particular patient in a practice where at least two difference surgeons use the same operating room equipment. After review the patients' file and determining the desired system characteristics, the surgeon may access the virtual operating room equipment GUI and change and save the desired settings to the virtual operating room equipment GUI prior to surgery. These saved changes may be automatically downloaded to the appropriate operating room equipment or loaded on to the operating room equipment manually by the surgeon or other designated personnel, such as a nurse, for example. By reviewing and choosing certain attributes in advance, the surgeon and/or designated personnel does not have to spend the time advancing through menus and choosing such changes directly on the operating room equipment, thus limiting the amount of time the operating room equipment is not otherwise being used for actual surgical procedures.

The use of the virtual operating room equipment GUI allows a surgeon to make setting changes not only from a location remote from the operating room equipment, but also outside the time(s) when the operating room equipment might otherwise be available for use. This may allow and encourage a surgeon to enter their own system preferences rather than instructing, generally in a verbal manner, other personnel to enter and make requested changes to the setup of the operating room equipment. By eliminating the need to have subordinates pre-program the operating room equipment, errors related to the entry of such data and the correspondent surgical errors that might be precipitated may be lessened or eliminated.

As would be appreciated by those skilled in the art, not only does the present invention allow for time savings when looking to modify operating room equipment, but allows for multiple users to each utilize the virtual operating room equipment GUI concurrently and may provide the ability of surgeons and/or designated assistants to store and/or upload preferences to the physical operating room equipment as needed.

By way of example, a cataract surgical practice may have a single WHITESTAR Signature® phacoemulsification system for use in surgery but may have three doctors involved in the practice. While one doctor is using the phacoemulsification system during surgery, either one or both of the remaining two surgeons may be utilizing the present invention to create stored setting which may be quickly loaded to the phacoemulsification system when it is time for they themselves to perform surgery. Indeed, as soon as the first surgeon is finished with the phacoemulsification system, a surgical assistant, for example, may load preferences stored by surgeon two which were created the night prior while surgeon two was reviewing information related to the patient involved in the forthcoming surgery. More commonly, however, surgeons will not need to adjust settings on a patient by patient basis, but will instead have individual preferences which may be saved and loaded onto the phacoemulsification system by the surgical staff correspondent to the change in the surgeon using the phacoemulsification system.

Figure 7:
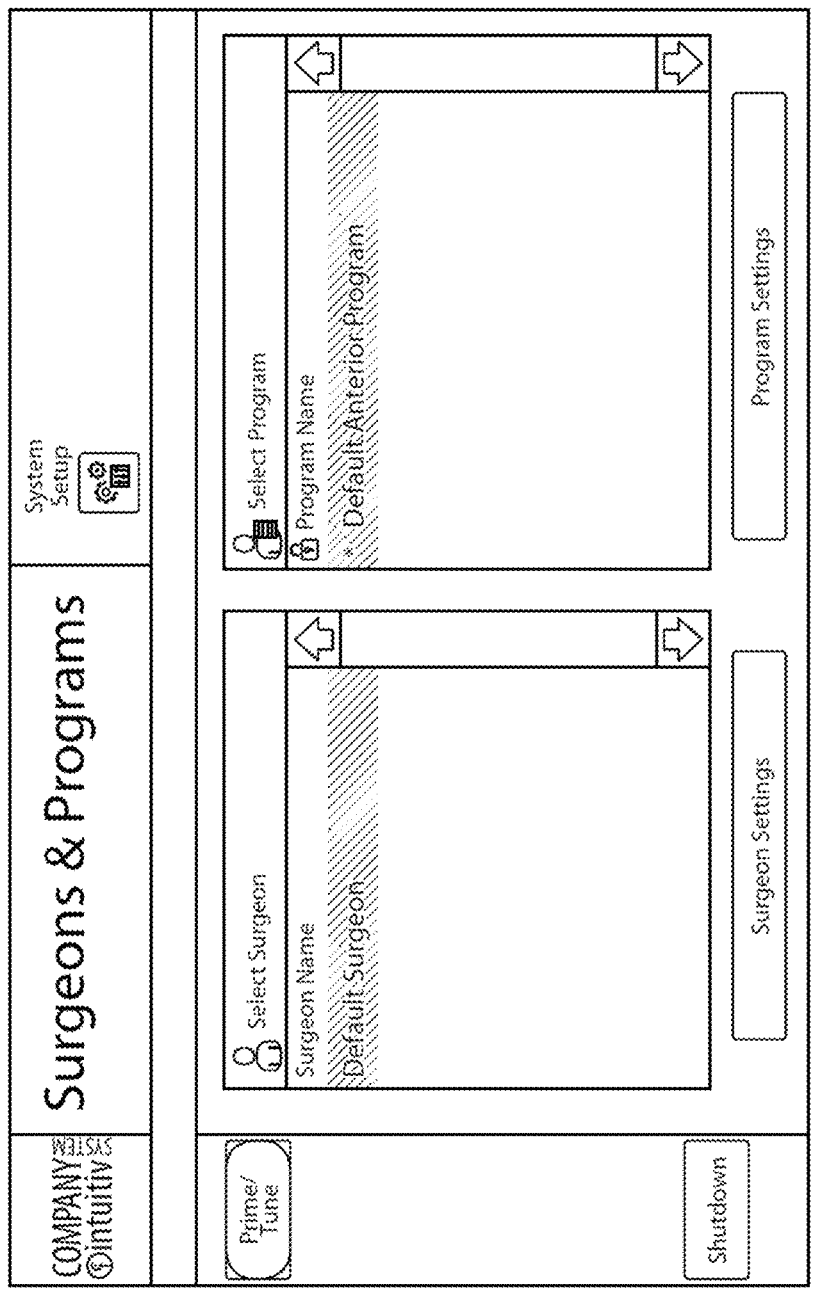
Figure 8:
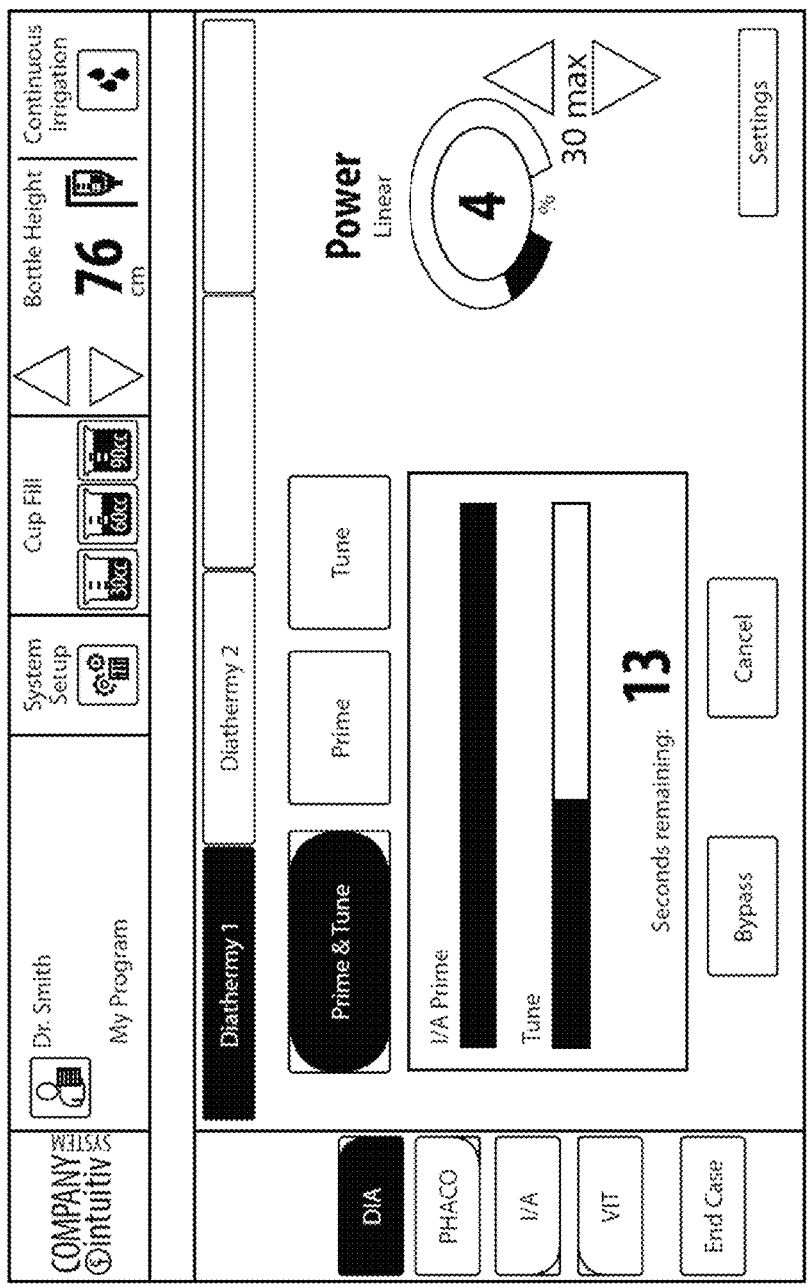
Figure 9:
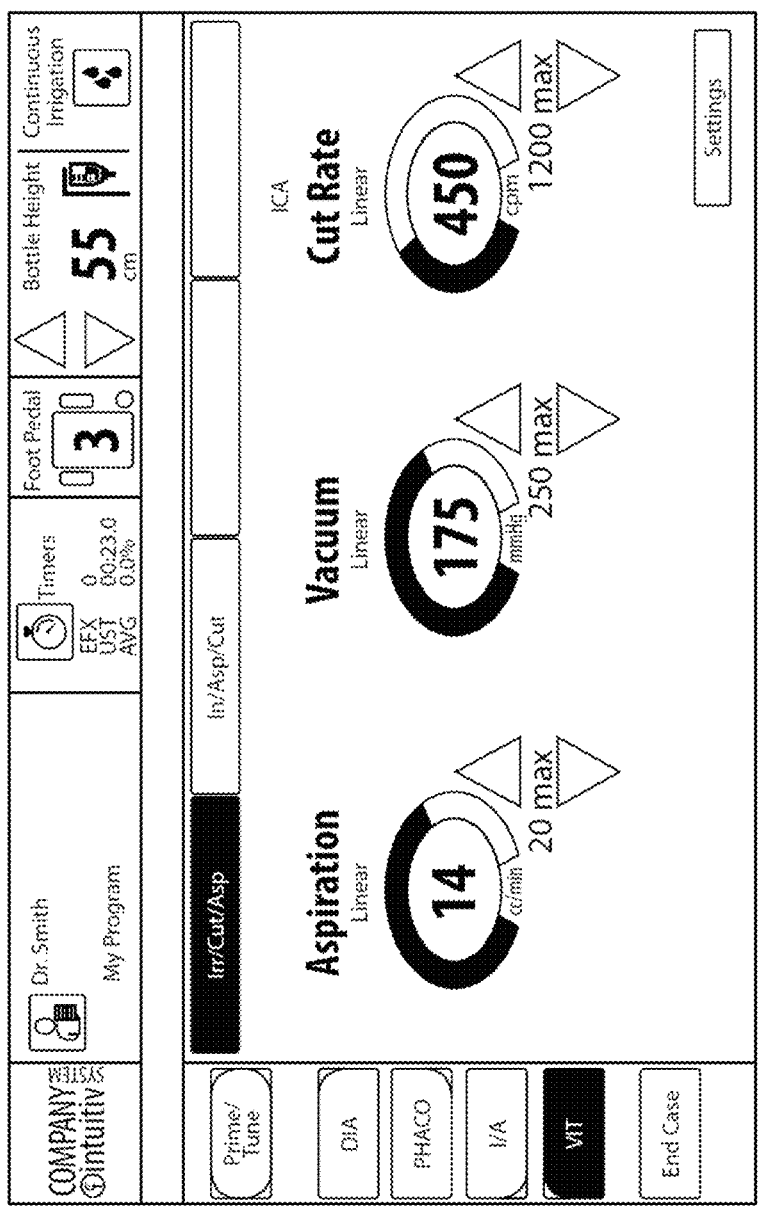
Figure 10:
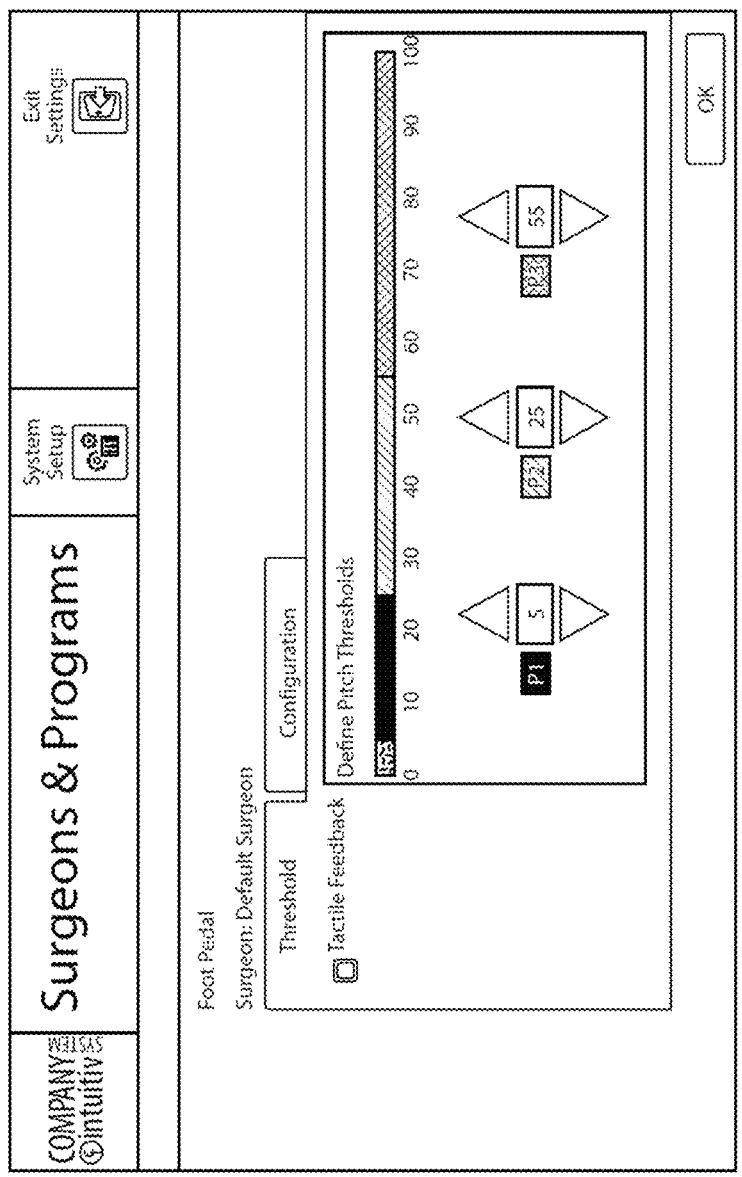
Figure 11:
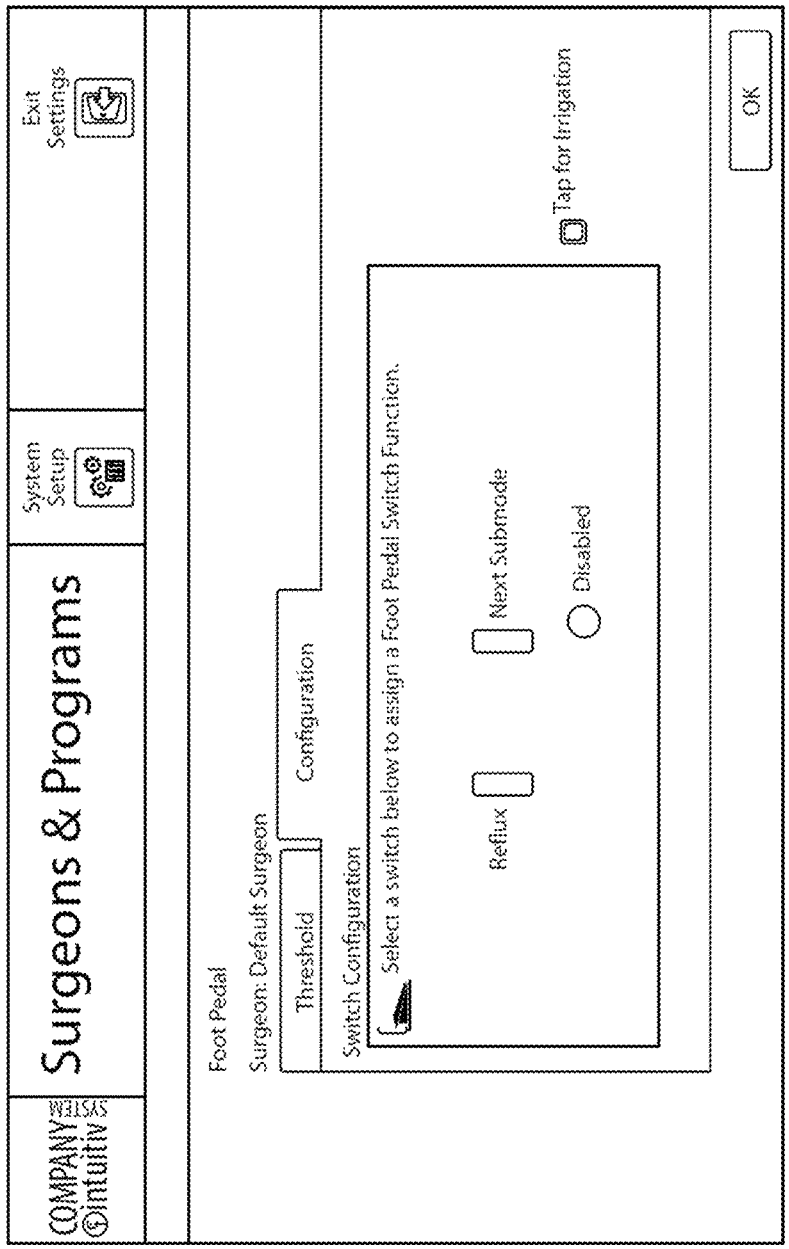
Figure 12:
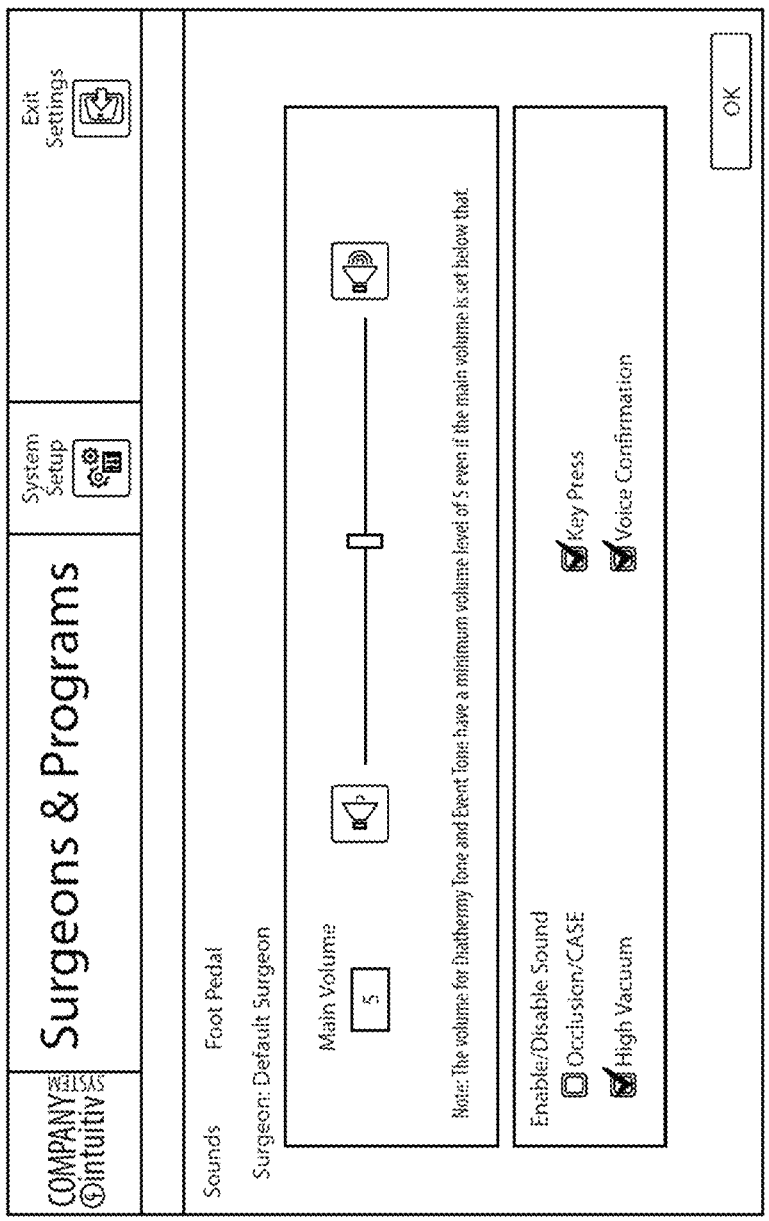
Figure 13:
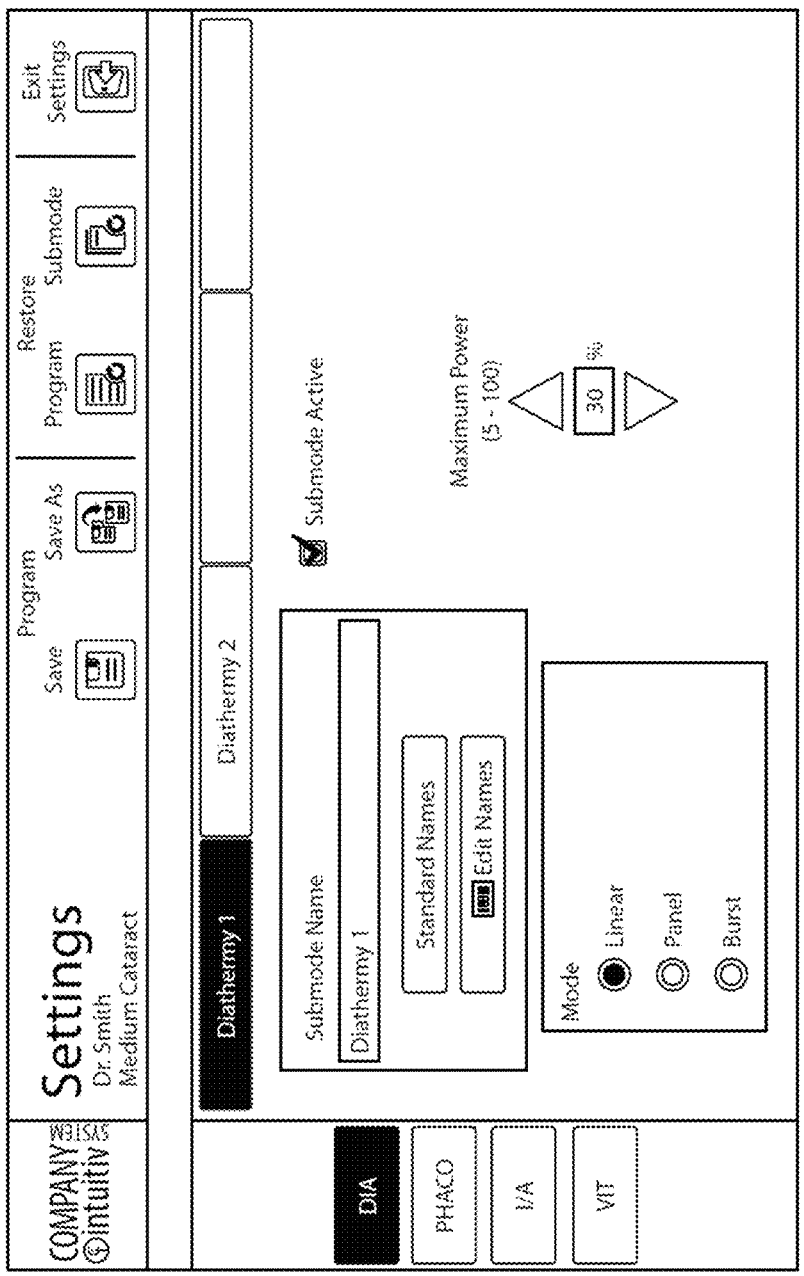
Figure 14:
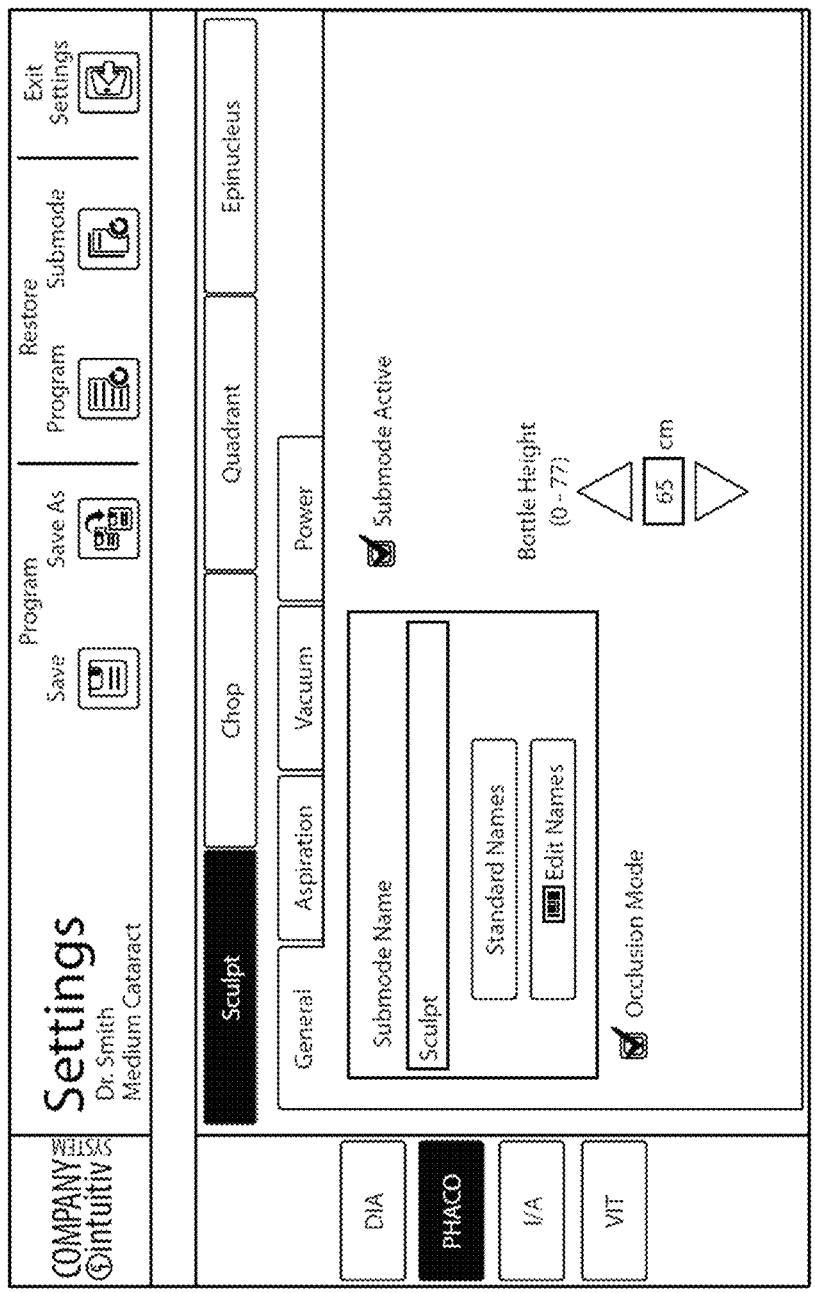
Figure 15:
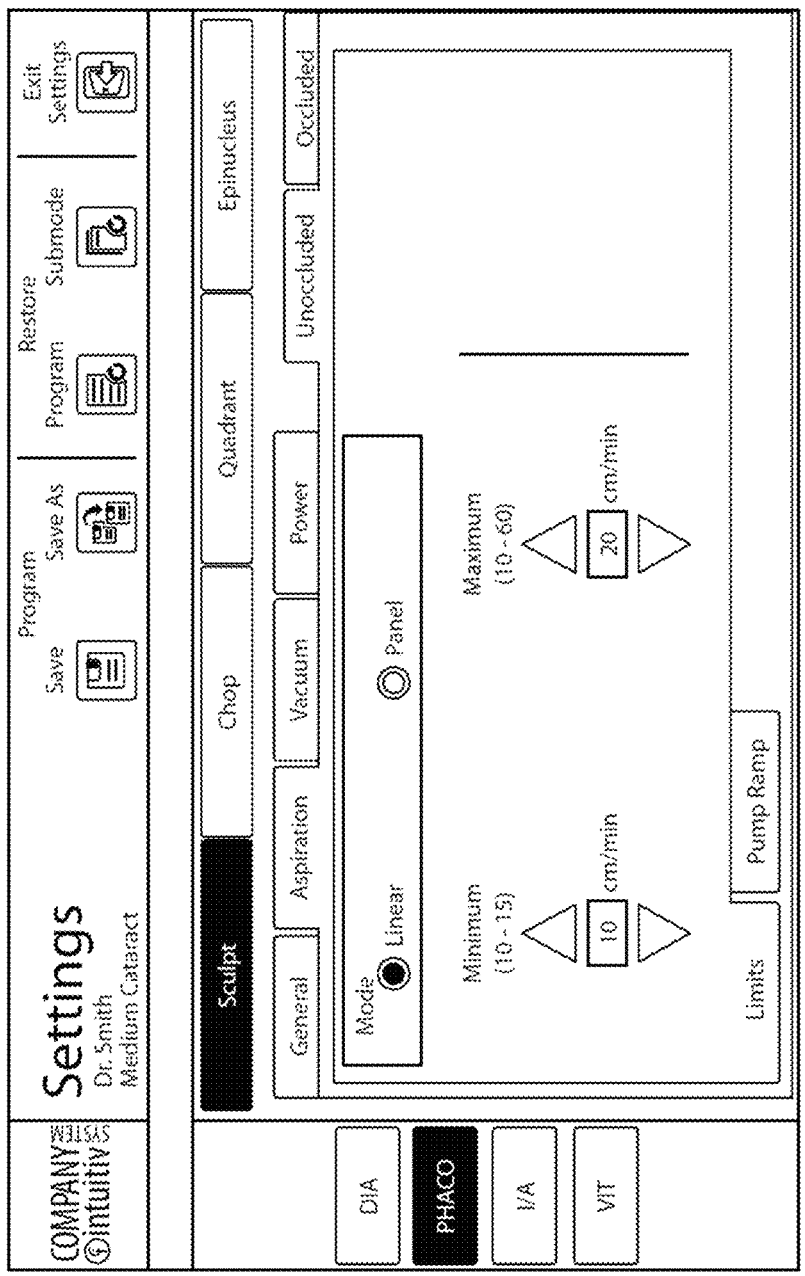
Figure 16:
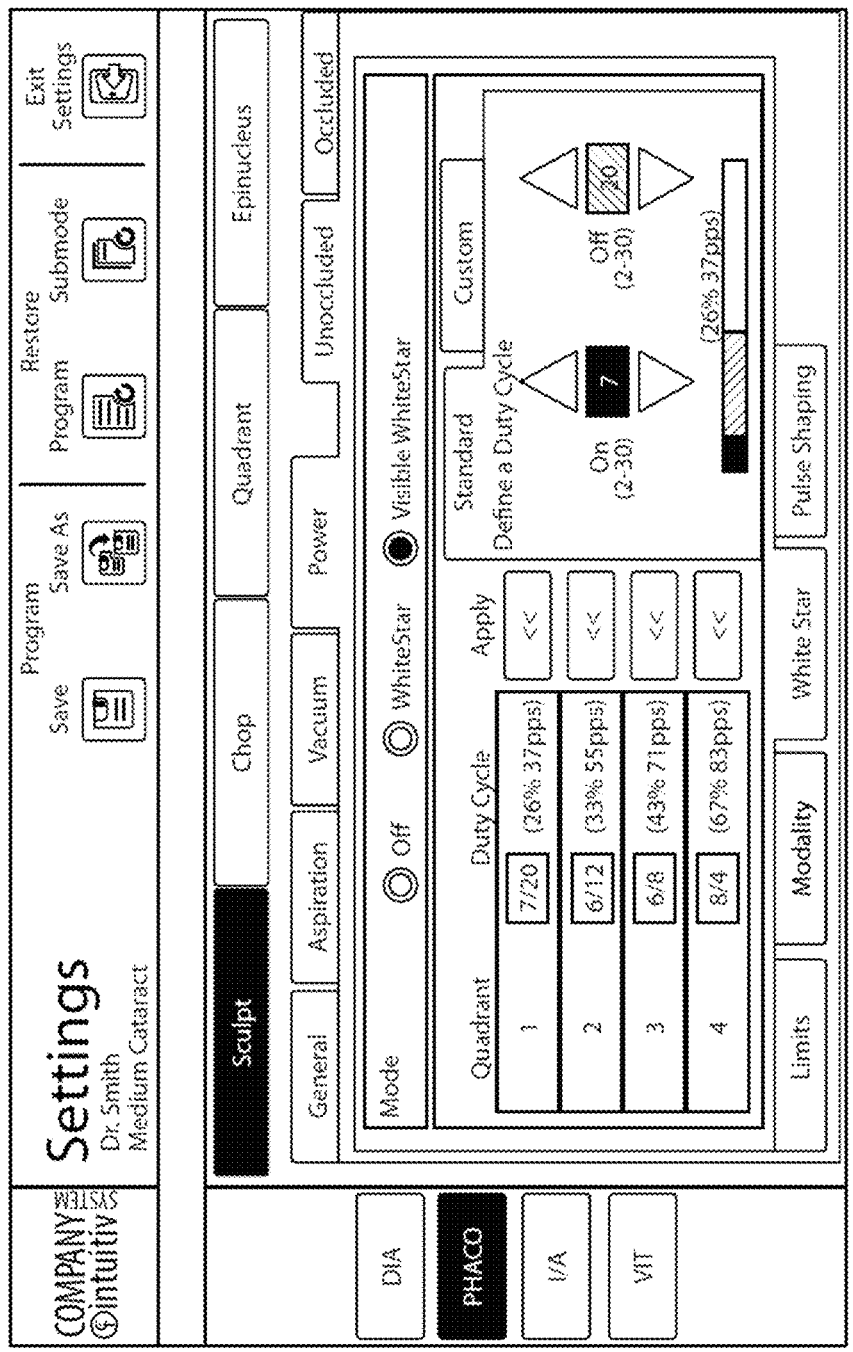
Figure 17:
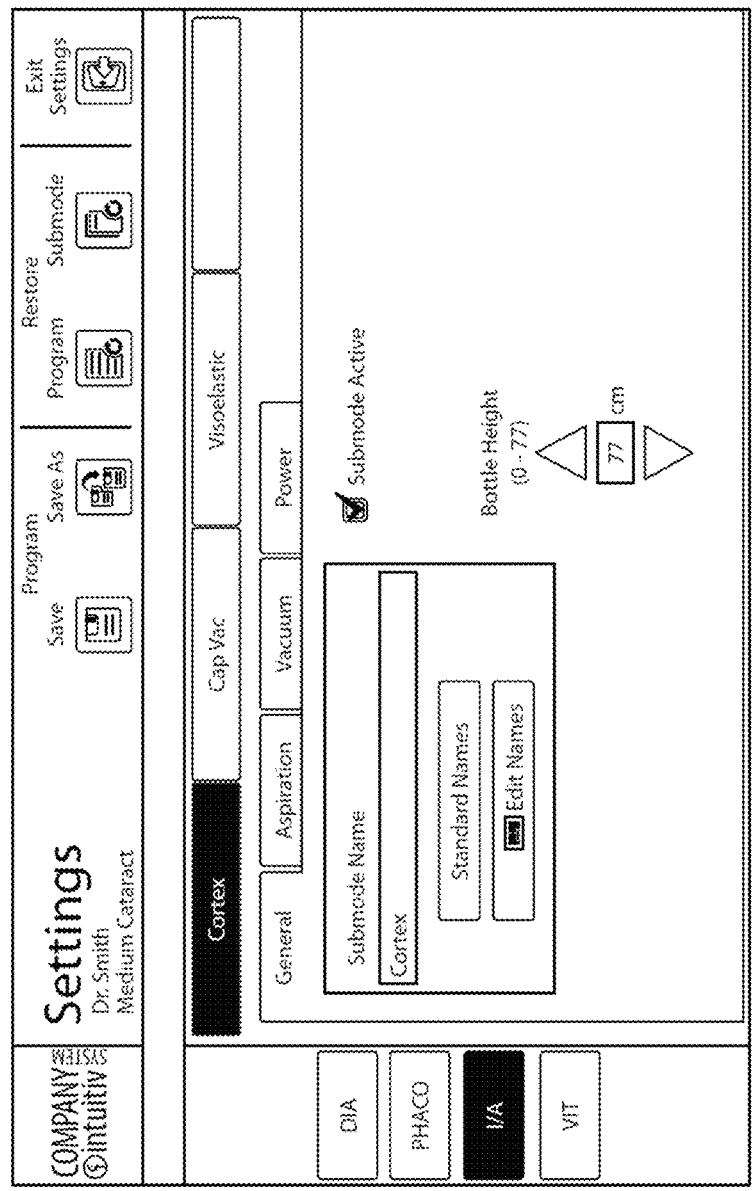
Figure 18:
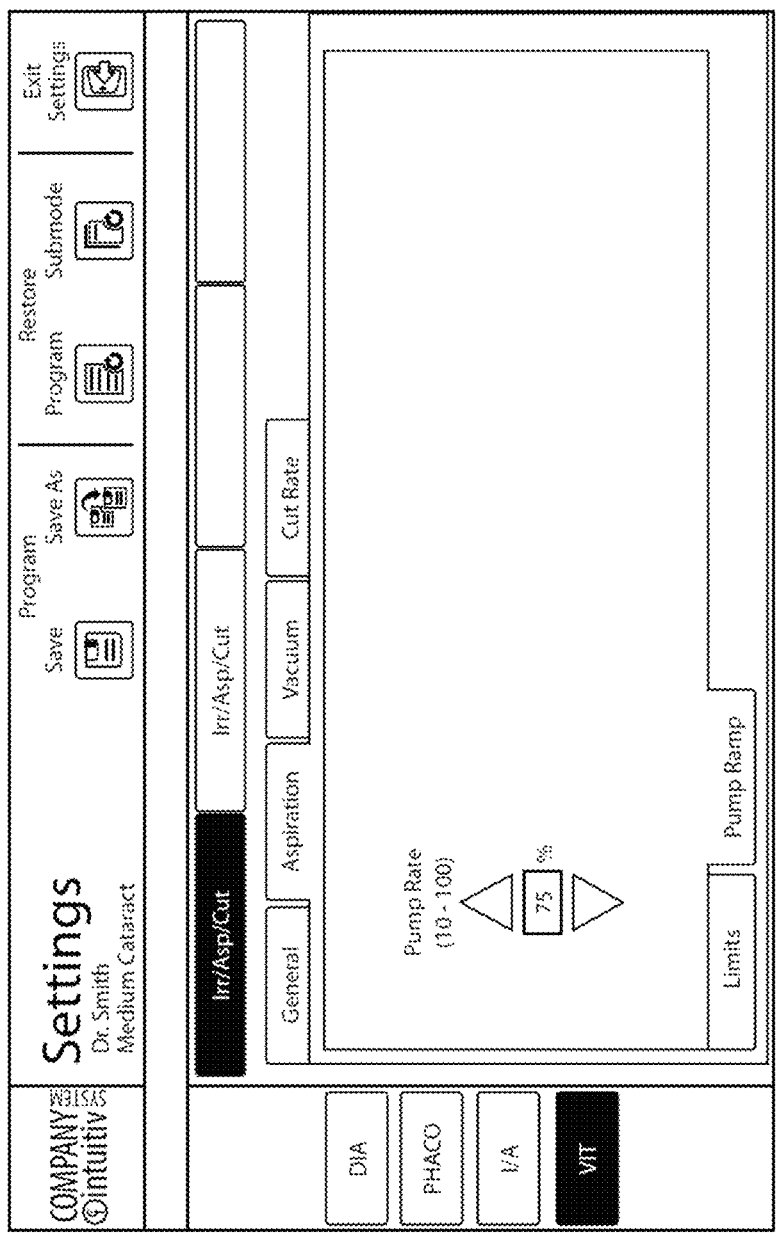
Figure 19:
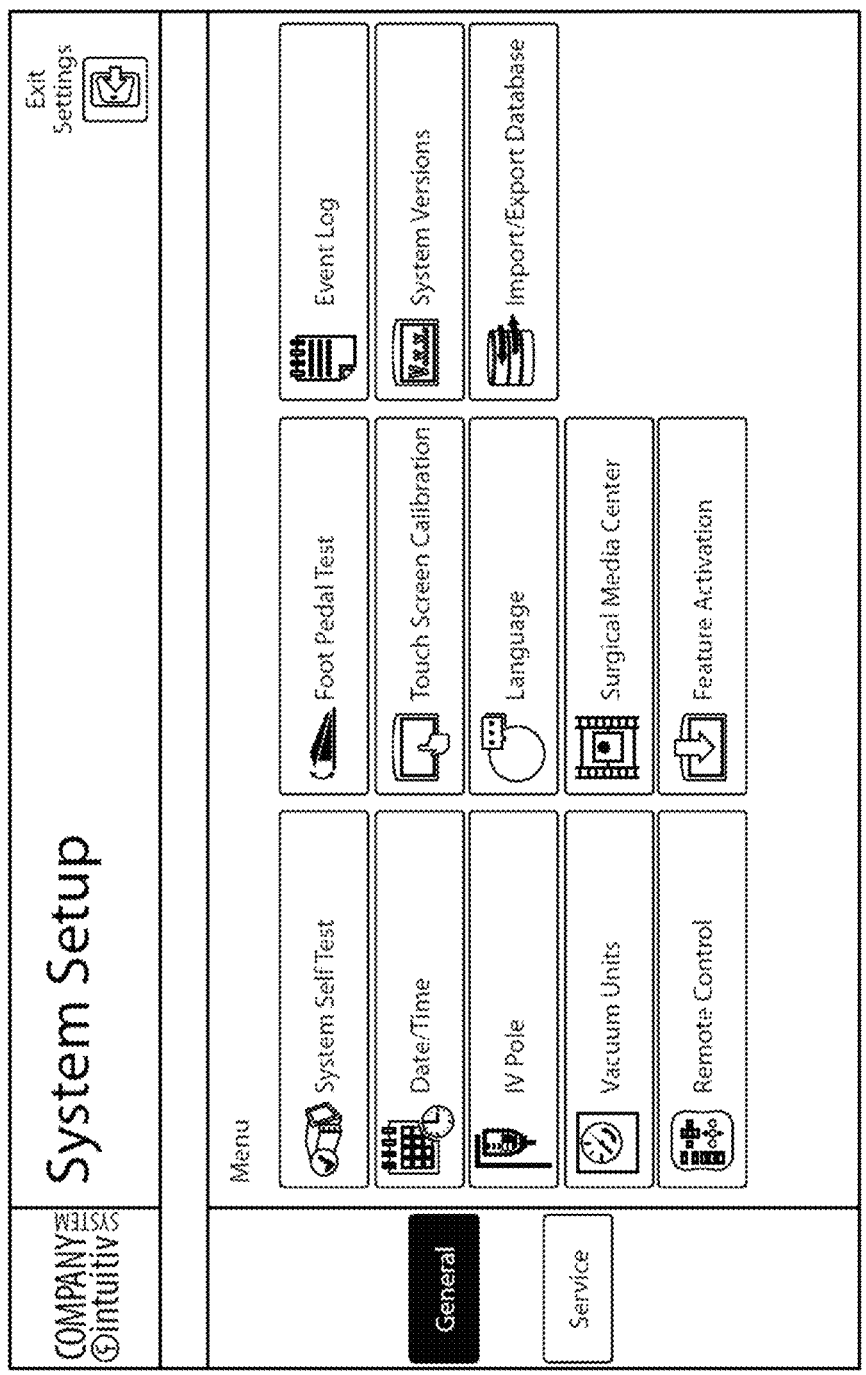
Figure 20:
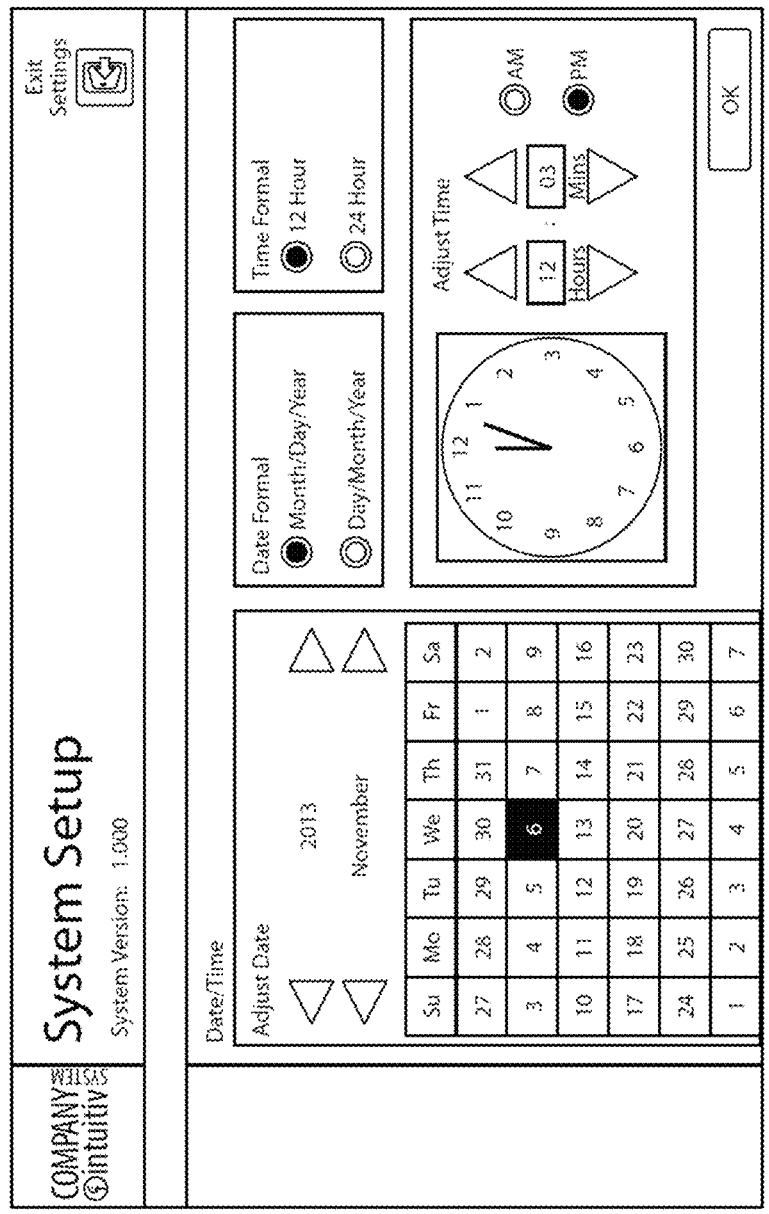
Figure 21:
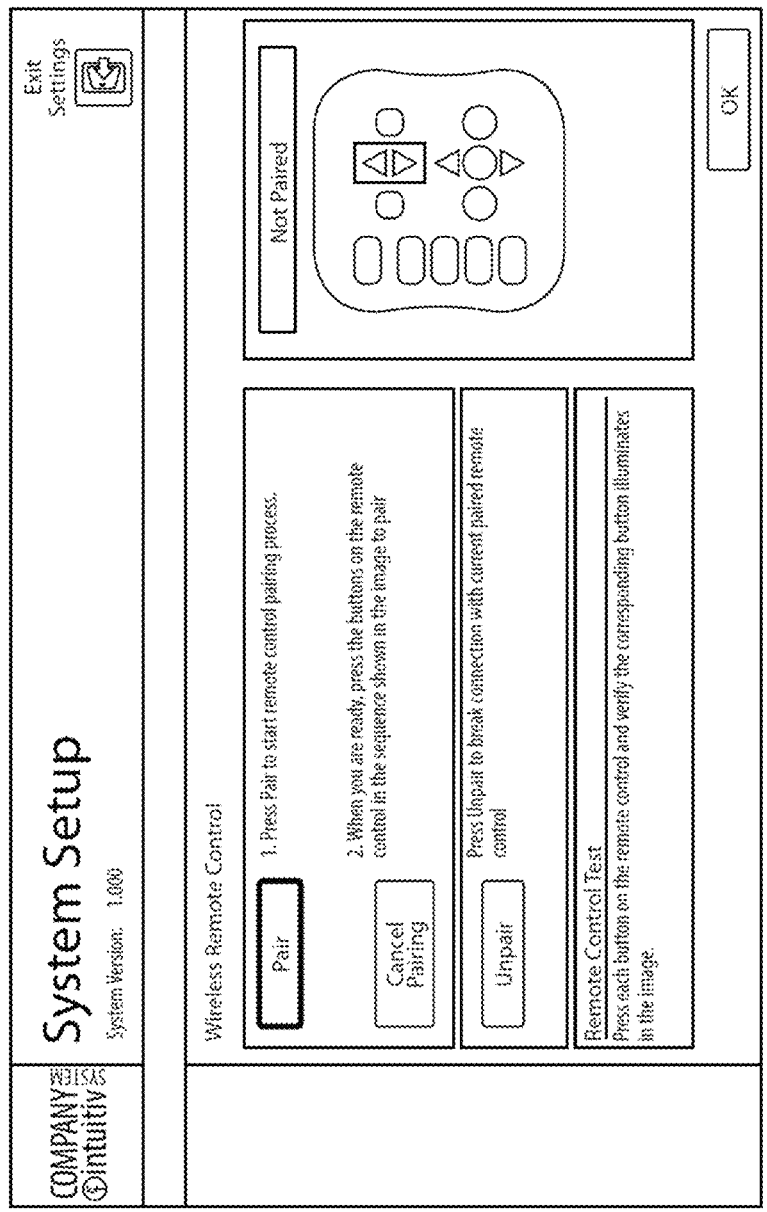
Figure 22:
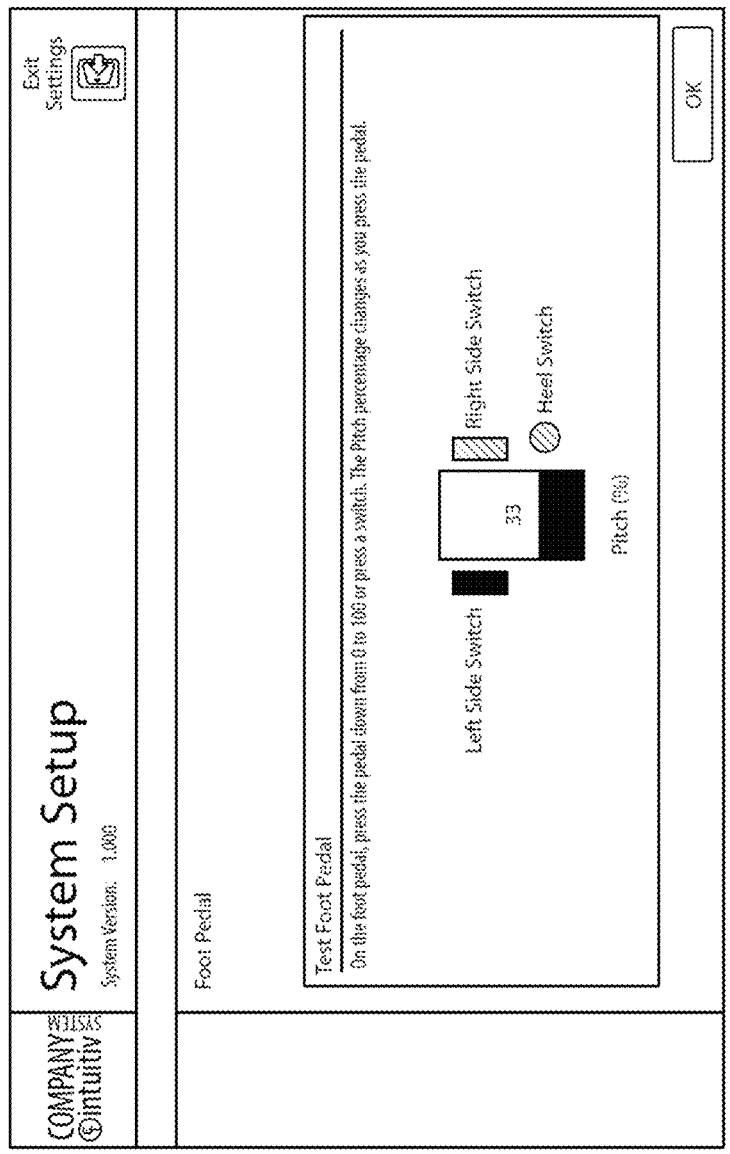

Referring back now to FIGS. 6-22, as described herein, a user may be presented the same GUI and associated functionality correspondent to a phacoemulsification system, such as the WHITESTAR Signature® phacoemulsification system, for example. As illustrated in FIG. 7, users and programs already associated with either the virtual operating room equipment GUI and/or the physical operating room equipment GUI may be present for selection. If "Dr. Smith" is selected, the virtual operating room equipment GUI may be prepopulated with prior entered settings as used by Dr. Smith as illustrated in FIG. 8, for example.

In an embodiment of the present invention, components generally associated with operating room equipment and in communication with the user terminal may be used and/or tested through the virtual operating room equipment GUI. For example, a foot pedal may be connected to a tablet computer at the home of a surgeon via known protocols, such as Bluetooth, for example, and may be in communication with the virtual operating room equipment GUI. In this way, a surgeon may adjust, preprogram, and/or refine the usage of the foot pedal through the virtual operating room equipment GUI rather than while in active surgery. Similarly, the surgeon can test the setup of a foot pedal and better understand it's functionality and/or sensitivity so as to provide a better use experience for the surgeon and, as a result, a better surgical outcome.

In the same vein, the virtual operating room equipment GUI may be deployed as a teaching and or sales tool to allow for surgeons to become comfortable with the operating room equipment prior to making a purchase decision. For example, a sales person may demonstrate the use of a foot pedal and the interaction with the virtual operating room equipment GUI which may further display virtual runtime statistics. Such a demonstration may be enhanced by allowing for the virtual operating room equipment GUI to run against a "virtual patient" in the form of a data set of information intended to simulate surgery. Such information may be gathered during an actual surgical procedure and/or may be created wholesale to simulate perceived issues, for example, which may be encountered during surgery, such as, for example, a sudden increase is aspiration pressure due to debris substantially blocking the aspiration tube. A virtual spike in pressure may provide the user the opportunity to test run possible solutions to the issue and thus learning from a virtual issue.

In an embodiment of the present invention, a single piece of operating room equipment may be present at an academic institution due to the high cost of the operating room equipment, for example, and the fact that use of operating room equipment in an academic environment does correspond to a consistent demand for surgical use as in commercial settings. Similarly, an academic setting may generally include the need for student use of operating room equipment periodically during the learning process and may be concentrated during certain times. For example, during an eight week semester teaching student to use a specific piece of operating room equipment, "hands-on" use may only be allowed during the final three weeks, resulting in a high density of demand on a single resource.

Thus, the present invention may allow each student to use and master the controls and interface of the operating room equipment using their own virtual operating room equipment. By way of example, each member of a class numbering 40 students may be interfacing with an assigned virtual piece of operating room equipment in real time during a professor led class. The number of users may only be limited by the cloud computing resources allocated to the system. As discussed above, the information surrounding the students' use of their virtual operating room equipment may be recorded, allowing not only for granular usage information to be recorded and evaluated by a third party, such as a professor, for example, but for final settings to be stored and applied to physical operating room equipment when used by the student.

Although the invention has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure, the protected scope of which is defined by the claims.

What is claimed is:

1. A system for providing a virtual interface for a surgical console, comprising:
   a network coupled computer with a processor and a data storage device storing instructions which, when executed on the processor, causes the computer to perform tasks including:
   obtaining information correspondent to a graphical user interface of a surgical console, wherein the graphical user interface provides access to a plurality of selectable predefined programs and the plurality of selectable predefined programs control at least one of phacoemulsification power, irrigation and aspiration provided by the surgical console;

populating a virtual graphical user interface resident on a first device remote from the surgical console based on the information correspondent to the graphical user interface of the surgical console, wherein the virtual graphical user interface provides access to the plurality of selectable predefined programs;

receiving, from a second device remote from the surgical console, a request to access the virtual graphical user interface;

providing access to the virtual graphical user interface in accordance with the received request;

collecting and storing information received from the second device;

providing the information received from the second device to the first device and the surgical console; and storing information from the second device locally on the surgical console for later use with a future operation procedure, wherein the information includes at least one program setting for at least one selectable predefined program of the plurality of selectable predefined programs.

2. The system of claim 1, wherein the surgical console is used for eye surgery.

3. The system of claim 1, wherein the virtual graphical user interface and the graphical user interface of the surgical console are identical.

4. The system of claim 1, wherein the surgical console includes a computer-based phacoemulsification system.

5. The system of claim 1, wherein the information correspondent to a graphical user interface of a surgical console includes diagnostic information of the surgical console.

6. A method for providing a virtual interface for a surgical console, comprising:

providing on a network coupled computer, having a processor and a data storage device, a virtual graphical user interface of a graphical user interface of a phacoemulsification surgical console, wherein the graphical user interface of the surgical console provides access to a plurality of selectable predefined programs, the plurality of selectable predefined programs control at least one of phacoemulsification power, irrigation and aspiration provided by the surgical console and the virtual graphical user interface provides access to the plurality of selectable predefined programs;

receiving from a remote device a request to access the virtual graphical user interface;

providing access to the virtual graphical user interface in accordance with the received request;

collecting and storing information received from the remote device; and storing information received from the remote device locally on the phacoemulsification surgical console for later use with a future operation procedure, wherein the information includes at least one program setting for at least one selectable predefined program of the plurality of selectable predefined programs.

7. The method of claim 6, wherein the information received from the remote device is transmitted to the phacoemulsification surgical console.

8. The method of claim 6, wherein the virtual graphical user interface is displayed in real time on the remote device.

9. The method of claim 6, wherein the virtual graphical user interface further comprises patient information stored prior to the received request.

10. The method of claim 9, wherein the patient information is obtained from the phacoemulsification surgical console.

* * * * *